(12) United States Patent
Faris (10) Patent No.: US 6,962,816 B2
(45) Date of Patent: Nov. 8, 2005

(54) HIGHLY CONTROLLABLE ELECTROPORATION AND APPLICATIONS THEREOF

(75) Inventor: Sadeg M. Faris, Pleasantville, NY (US)

(73) Assignee: Reveo, Inc., Elmsford, NY (US)

(*) Notice: Subject to any disclaimer, the term of this patent is extended or adjusted under 35 U.S.C. 154(b) by 73 days.

(21) Appl. No.: 10/755,709

(22) Filed: Jan. 12, 2004

(65) Prior Publication Data

US 2004/0241859 A1 Dec. 2, 2004

Related U.S. Application Data

(60) Provisional application No. 60/439,387, filed on Jan. 10, 2003.

(51) Int. Cl.$^7$ ............................................. C12N 15/87
(52) U.S. Cl. .................................... 435/461; 435/285.2
(58) Field of Search .............................. 435/461, 285.2

(56) References Cited

PUBLICATIONS

Fang et al., International Journal of Pharmaceutics, vol. 235 (2002) pp. 95–105.*

* cited by examiner

*Primary Examiner*—James Ketter
(74) *Attorney, Agent, or Firm*—Ralph J. Crispino

(57) ABSTRACT

The controllable electroporation system and method described herein allows control over the size, the number, the location, and the distribution of aqueous pores, thus increasing flexibility of use. The herein described system and method for controllable electroporation generally employs at least two actuating sub-systems and sub-processes. One sub-system and sub-process employs a relatively broad effect in order to weaken the membrane, a broad effect sub-system. Another sub-system and sub-process employs a relatively narrow effect in order to localize the position of the pore in the membrane, a narrow effect sub-system.

51 Claims, 7 Drawing Sheets

HIGHLY CONTROLLABLE ELECTROPORATION AND APPLICATIONS THEREOF

RELATED APPLICATIONS

This application claims the benefit under 35 U.S.C. § 119(e) of U.S. Provisional Application No. 60/439,387 filed on Jan. 10, 2003, which is herein incorporated by reference

BACKGROUND

The membrane of a cell serves the vital function of partitioning the molecular contents from its external environment. The membranes are largely composed of amphiphilic lipids, which self-assemble into highly insulating structures and thus present a large energy barrier to trans-membrane ionic transport.

However, the lipid matrix can be disrupted by a strong external electric field leading to an increase in trans-membrane conductivity and diffusive permeability, a well-known phenomenon known as electroporation. These effects are the result of formation of aqueous pores in the membrane. More particularly, electroporation process involve permeation of cell membranes upon application of short duration electric field pulses, traditionally between relatively large plate electrodes (Neumann, et al., Bioelectrochem Bioenerg 48, 3–16 (1999); Ho, et al., Crit Rev Biotechnol 16, 349–62 (1996)).

Figure 2A:
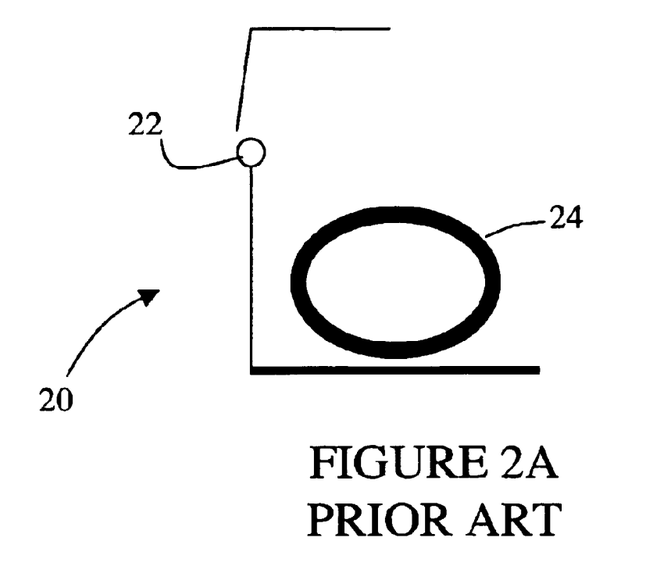
FIGS. 2A and 2B show operation of conventional electroporation systems.
Figure 2B:
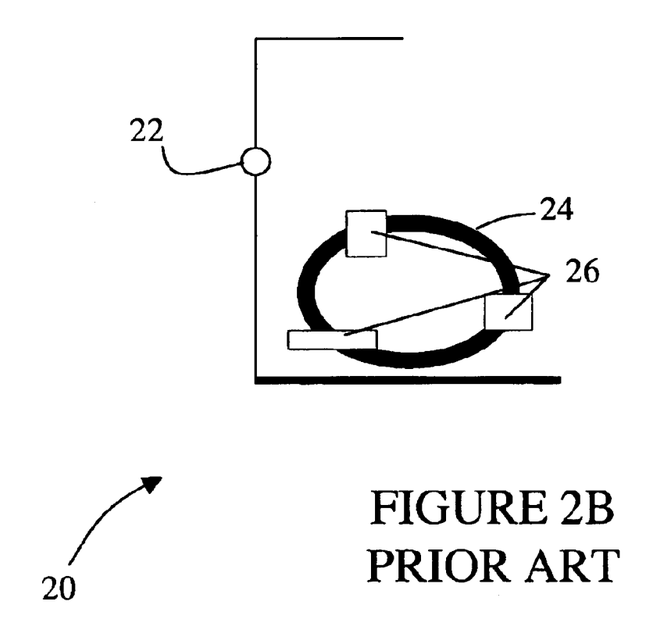

For example, FIGS. 2A and 2B show a conventional electroporation system 20, whereby impression of an electric field (e.g., shown by closing a circuit 22) creates random pores 26 in a cell membrane 24. The distribution of such pores, in terms of size and number only, is determined by the strength and duration of the applied electric field. The stronger and the longer the electric field is applied, the more numerous and larger the pores are. However, the exact location of such pores cannot be controlled, and thus the final distribution of pores is somewhat random. Researchers lose control over where compounds are introduced into the intracellular matrix, an oft-important ingredient in biochemical pathways. Thus researchers often have to rely on the cell's own natural mechanisms, a far slower and difficult process to utilize.

Electroporation is used for introducing macromolecules, including DNA, RNA, dyes, proteins and various chemical agents, into cells. Large external electric fields induce high trans-membrane potentials leading to the formation of pores (e.g., having diameters in the range of 20–120 nm). During the application of the electric pulse, charged macromolecules, including DNA, are actively transported by electrophoresis across the cell membrane through these pores (Neumann, et al., Biophys J 712 868-77 (1996)). Uncharged molecules may also enter through the pores by passive diffusion. Upon pulse termination, pores reseal over hundreds of milliseconds as measured by recovery of normal membrane conductance values (Ho, 1996, supra).

This procedure is often used in laboratory settings to inject chemical and biological compounds into a cell, avoiding the reliance on the cell's own protein receptors and trans-membrane channels for transport across the cell membrane. This allows researchers to easily study the biological affect of compounds, be it a potentially life-saving cancer drug or a deadly biological toxin. However, current electroporation techniques are limited.

Therefore, it would be desirable to provide a method and system to overcome these and other limitations of conventional electroporation.

SUMMARY

The above-discussed and other problems and deficiencies of the prior art are overcome or alleviated by the several methods and apparatus of the present invention for controllable electroporation. The controllable electroporation system and method allows control over the size, the number, the location, and the distribution of aqueous pores, thus increasing flexibility of use. The herein described system and method for controllable electroporation generally employs at least two actuating sub-systems and sub-processes. One sub-system and sub-process employs a relatively broad effect in order to weaken the membrane, a broad effect sub-system. Another sub-system and sub-process employs a relatively narrow effect in order to localize the position of the pore in the membrane, a narrow effect sub-system.

The above-discussed and other features and advantages of the present invention will be appreciated and understood by those skilled in the art from the following detailed description and drawings.

DETAILED DESCRIPTION

Figure 1A:
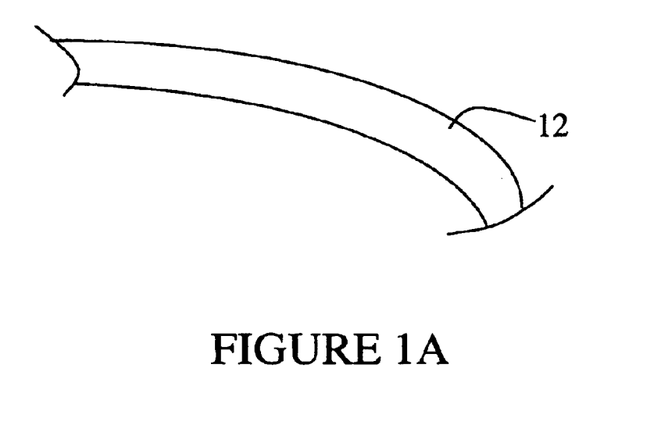
FIGS. 1A and 1B show operation of the controllable electroporation system described herein.
Figure 1B:
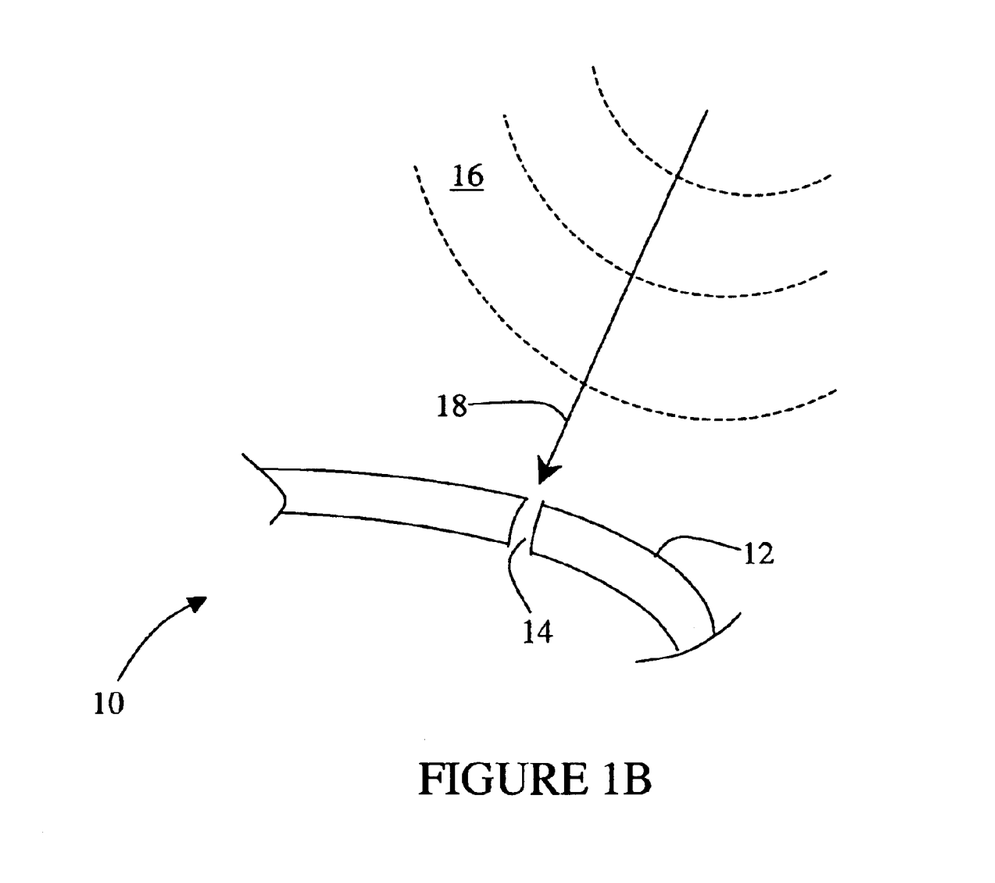

Herein described is an electroporation system and method providing control over the size, the number, the location, and the distribution of aqueous pores, thus increasing flexibility of use. Referring generally to FIGS. 1A and 1B, the herein described system 10 and method for controllable electroporation of a membrane 12 generally employs at least two actuating sub-systems and sub-processes. FIG. 1A shows a portion of a membrane 12, and FIG. 1B shows the controllable electroporation system 10 described herein.

Note that in general, one of the actuating sub-systems alone will not suffice to open or create a pore 14 in the membrane-both actuating sub-systems are employed, thereby functioning in a similar manner as a logical "and" gate. A broad effect sub-system 16 employs a relatively broad effect in order to weaken the membrane, and the narrow effect sub-system 18 employs a relatively narrow effect in order to localize the position of the pore 14 in the membrane 12. Employing both the broad effect sub-system 16 and the narrow effect sub-system 18 enables highly localized and controlled electroporation and hence opening of pore 14.

Therefore, for example as compared to conventional electroporation processes of cellular membranes, described in the Background and with respect to FIGS. 2A and 2B, in addition to the applied electric field of conventional electroporation technology, the herein disclosed electroporation system and method employs a narrow effect sub-system 18 directed at a specific location on the cellular membrane, enabling positional control over the pore 14. The narrow effect sub-system 18 will excite the phospholipid molecules, thus reducing the amount of energy required from the broad effect sub-system 16 to create the aqueous pores. Thus, for example, a very weak electric field can be applied to a system, in which typically, electroporation would not occur. However, this weak electric field can open aqueous pores in places of the cellular membrane already excited by the laser beam.

The broad effect sub-system or sub-process 16 may be selected from any suitable membrane weakening systems and/or processes. Such weakening systems and/or processes may be selected from the group consisting of electric fields (in certain preferred embodiments uniform electric fields), microwave energy, other electromagnetic radiation, relatively low energy laser beams (i.e., lower energy than that required to commence random electroporation), or any combination comprising at least one of the foregoing weakening systems and/or processes. The energy magnitude of the broad effect sub-system or process 16 is generally lower than the energy magnitude of conventional electroporation systems whereby random pore opening occur. Further, the area (e.g., cross-sectional area) of the weakening systems and/or processes 16 generally encompasses an area larger than the desired pore size. In certain embodiments, this area encompasses the entire cell membrane or an array of cell membranes. In other embodiments, this area is a region of a membrane.

The narrow effect sub-system or sub-process 18 may be selected from any suitable membrane pore position localization systems and/or processes. Such position localization systems and/or processes may be selected from the group consisting of laser beams, electrode tips, or any combination comprising at least one of the foregoing position localization systems and/or processes. The area (e.g., cross-sectional area) of the position localization systems and/or processes 18 is generally narrow, e.g., corresponding to the desired dimensions of the pore opening. Thus, for example, controlled pore openings having of sub-micron or nanometer (e.g., 1–100 nm) magnitude are enabled, since existing and developing laser and electrode tip technologies are capable of such sub-micron-scale and nano-scale dimensions.

Applications

Cell Injection

The herein described controllable electroporation system and process may be used to inject macromolecules, including DNA, RNA, dyes, proteins and various chemical agents, in a controlled manner. Without intending to limit the applications of the present controllable electroporation system, FIGS. 3A–5B show various embodiments of cell pore opening systems employing the controllable electroporation system.

Figure 3A:
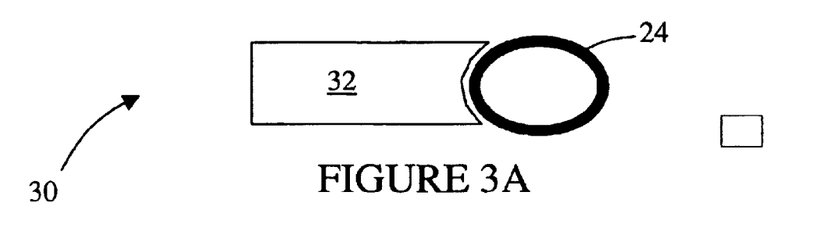
FIGS. 3A–3D show a general embodiment of a cell injection system.

Referring now to FIGS. 3A–3D, a system 30 is shown for controllable injecting macromolecules into a cell. FIG. 3A depicts the system 30 including a mechanism 32 for holding a cell 24. Mechanism 32 is a suitable microrobotic device including associated microsystems as are generally known in the biotechnology arts. Such as device 32 preferably is capable of holding individual cells or controlled groups of cells. Further, mechanism 32 may also be used to obtain biological, electrical, optical, or other data from the cell 24.

Figure 3B:
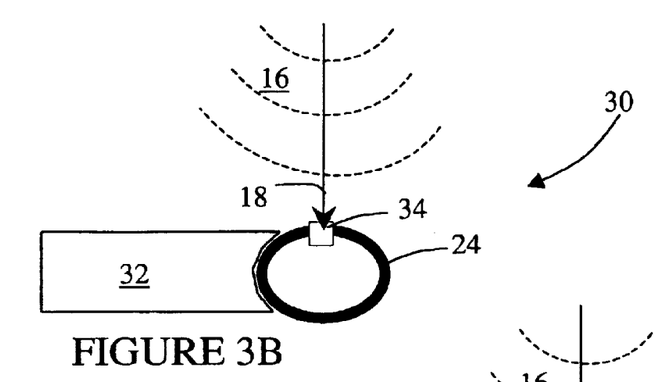

Referring now to FIG. 3B, the system 30 is shown including the mechanism 32 holding the cell 24, and a controllable electroporation system including the broad effect sub-system 16 and the narrow effect sub-system 18, whereby the narrow effect sub-system 18 is focused at a location on the cell 24 to induce opening of a pore 34.

Figure 3C:
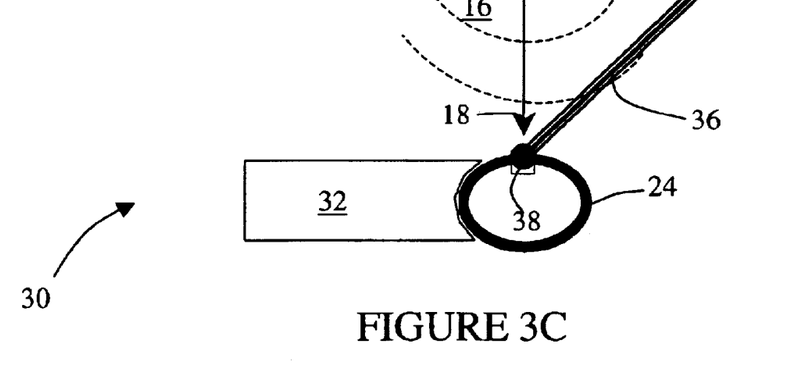
Figure 3D:
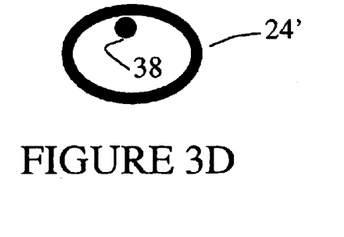

Referring now to FIG. 3C, a macromolecule 38 is introduced, for example, via a nano-nozzle or other suitable injection device 36. When the narrow effect sub-system 18 and/or the broad effect sub-system 16 is removed, the pore will close, resulting in cell 24' having macromolecule 38 therein.

Figure 4A:
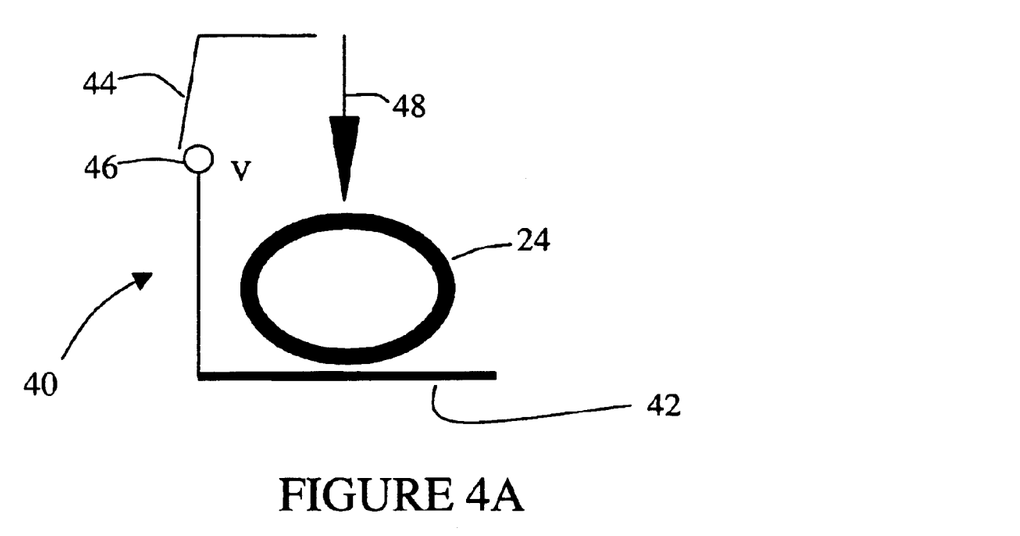
FIG. 4A–4B shows an example of a cell injection system.
Figure 4B:
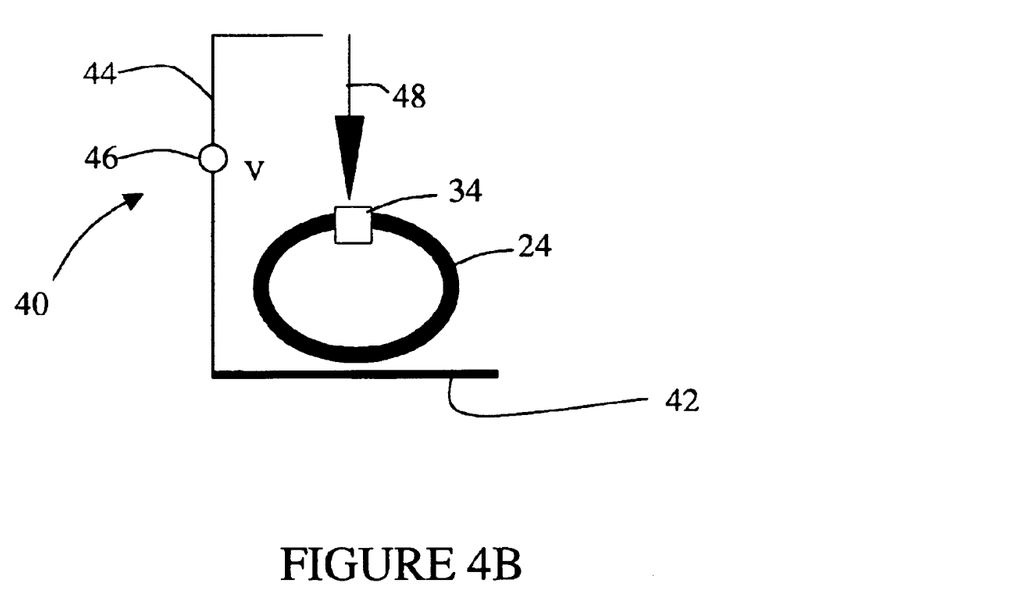

FIGS. 4A and 4B show one embodiment of a controllable electroporation system 40 for introducing controllably opening a pore 34 in a cell 24, e.g., for introduction of macromolecules as described above. The system 40 includes a broad effect sub-system in the form of an electric field producing apparatus 42, 44, 46, and a laser beam 48 from a suitable source (not shown). The electric field producing apparatus is in the form of an electrode plate 42 coupled to a switchable (via a switch 44) voltage source 46. As shown, the laser beam may be focused, and the electric field applied to active the pore opening mechanism, akin to a logical "and" circuit as described above.

With the system and method described with respect to FIGS. 3A–3D and 4A–4B, researchers could only expose a few cells in a tissue construct to a biological compound and observe how the signal is propagated to its neighboring cells. Alternatively, researchers could study if asymmetric cells such as neurons and gastrointestinal mucosa cells react differently to compounds injected at different places.

Figure 5A:
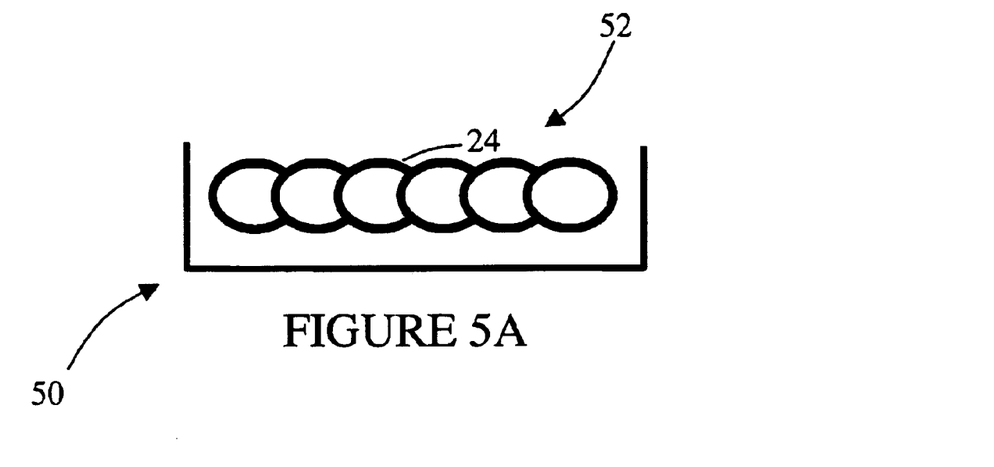
FIG. 5A–5B shows an example of a cell injection system for an array of cells.
Figure 5B:
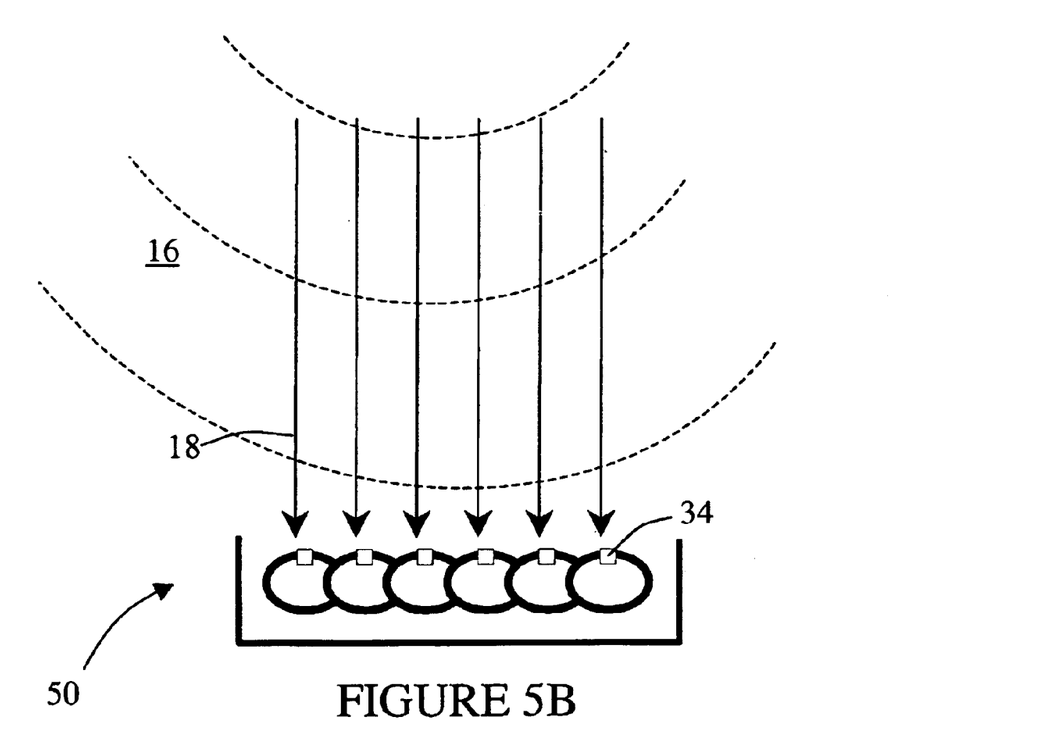

Referring now to FIGS. 5A and 5B, a system 50 is shown that operates similar to that of FIGS. 3A–3D or 4A–4B in conjunction with an array 52 of cells 24. When the broad effect sub-system 16 and the narrow effect sub-system 18 are operated, pores 34 are formed in the cells 24. Such pores may be used for selective introduction of macromolecules into the cells 24.

Separation Device

Referring now to FIGS. 6–10, various embodiments of filtration/separation devices are provided using the controllable electroporation system herein.

Figure 6:
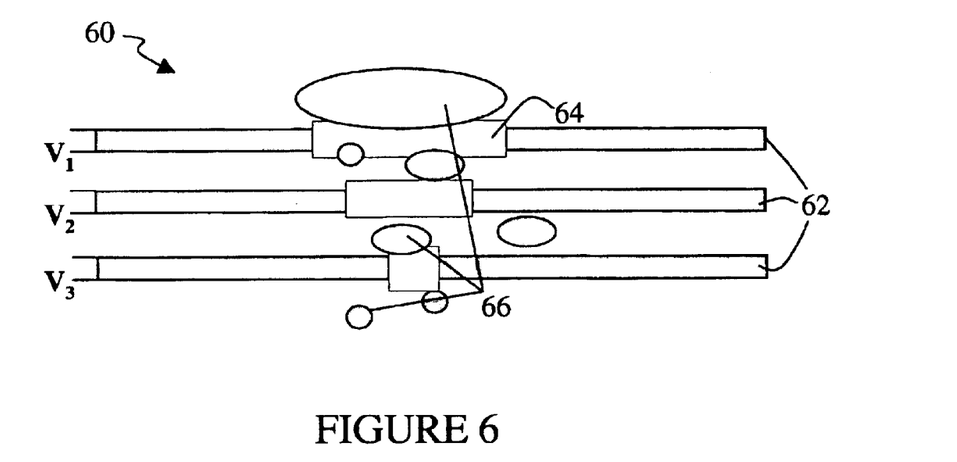
FIG. 6 shows a separation device using multi-phospholipid layers and electroporation.

FIG. 6 depicted one embodiment of a system 60, e.g., a molecular sieve. System 60 includes plural membrane layers 62, e.g., phospholipid bilayers. Each membrane layer 62 may be subject to a narrow effect sub-system during application of the broad effect sub-system, alternatively the location of the pores 64 may be predetermined upon assembly and or manufacture, e.g., with suitable micro- or nano-defects, or may be identical whereby different voltage levels at each layer determined the pore size. Application of different voltages (e.g. V1, V2 and V3) at each layer creates a filter gradient from large pores 64 to small pores 64, allowing passage of molecules 66 through suitable layers.

Using a phospholipid bilayer, which is extremely cheap to manufacture, the same filter 60 can be used repeatedly and adapted for any size requirements using electroporation and carefully controlling the electric field that is applied. Instead of depending on multiple filters, a single filter could be used and configured for any situation.

Figure 7:
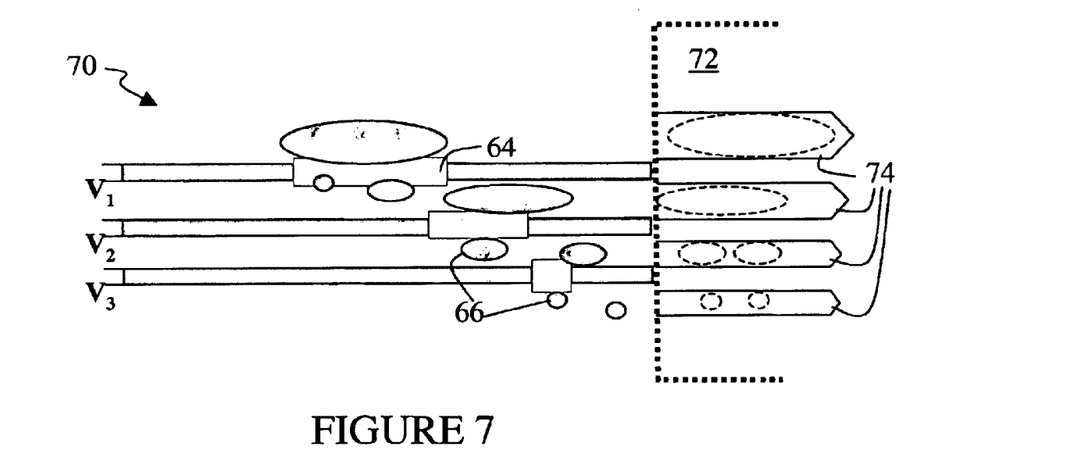
FIG. 7 shows a separation device using multiple layers, electroporation and a microfluid array.

Referring to FIG. 7, a system 70 is shown with a molecular sieve functioning similar to that of FIG. 6 associated with a biochip array 72 having channels 74 therein. Channels 74 may serve to collect macromolecules and molecules at each level based on size. Further, channels 74 may incorporate or be associated with a gradient system, e.g., pressure, thermal, electrical, or other gradient to induce macromolecules and molecules toward the array 72. Array 72 may be any suitable microfluidic or nanofluidic device. For example, methods of manufacturing such devices are described in Reveo Inc. PCT Application No. PCT/US03/37304 filed Nov. 30, 2003 entitled "Three Dimensional Device Assembly and Production Methods Thereof", which is incorporated by reference herein.

Figure 8:
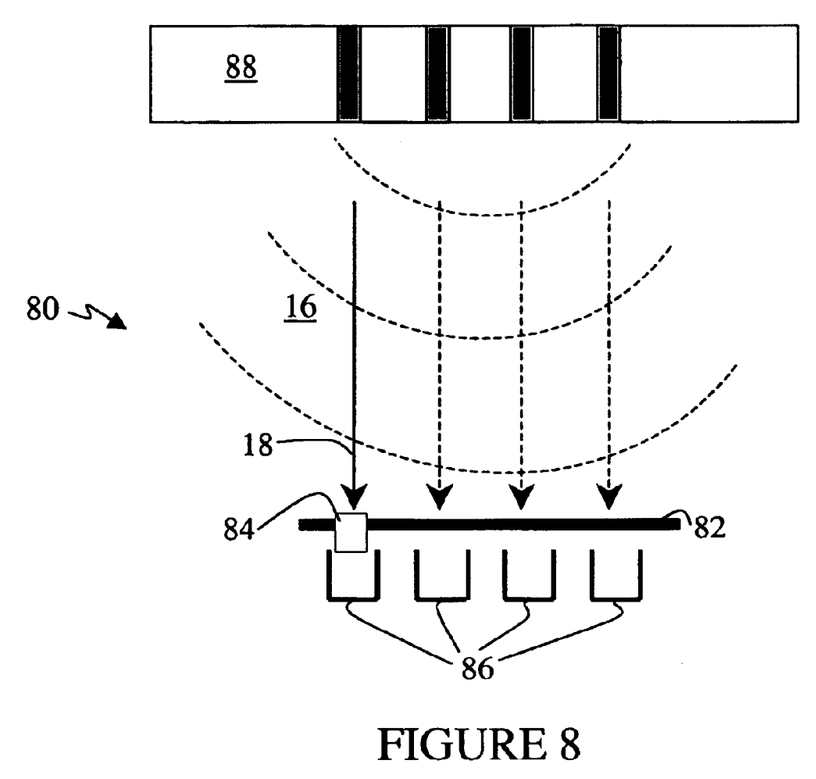
FIG. 8 shows a separation device using a single layer capapble of having different pores at different locations.

FIG. 8 shows another example dynamic filtration device, wherein an array of lasers provides positional control over the pore openings. FIG. 8 shows a filtration system 80 including a membrane layer 82 associated with a broad effect energy sub-system 16 and a narrow effect sub-system 18. For example, the narrow effect sub-system 18 may be generated with a laser array 88. Alternatively, instead of an array of lasers 88, a beam steering device may be incorporated, allowing use of only one laser source. When a laser is activated from the array associated with a certain position on the membrane 82, a pore 84 will open. The size of the pores may be controlled by predetermined membrane characteristics, area or magnitude of the narrow effect energy sub-system, or magnitude of the broad effect energy sub-system.

Cells, proteins, enzymes, DNA molecules, RNA molecules, and other macromolecules or molecules may be collected via an array of containers 86, e.g., on a suitable microfluidic device. Thus, separation device 80 may be made extremely compact and highly flexible for any purpose.

Figure 9:
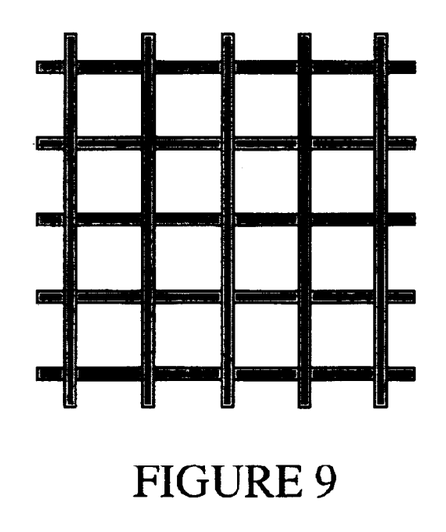
FIG. 9 shows an exemplary electrode grid that may be used in various embodiments described herein.

FIG. 9 shows an example of an electrode suitable for providing the broad effect energy sub-system in various embodiments shown herein. By providing electrodes in a grid pattern, a suitable field generating system may be provided to allow access for various purposes including the narrow effect sub-system, macromolecule introduction, filtration, or any other purpose.

In addition to filtering based on size, the aforementioned separation devices may also separate on the basis of ionic charge, since the applied voltage will drive only one type of ions across the membrane.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A system for controllable electroporation of a membrane comprising:
   a broad effect sub-system for providing broad energy to the membrane and
   a narrow effect sub-system for providing narrow energy to the membrane,
   wherein a pore is opened or created at a position corresponding to the position of the narrow energy.

2. The system as in claim 1, wherein the broad effect sub-system is selected from the group of weakening systems consisting of electric fields, microwave energy, other electromagnetic radiation, low energy laser beams, or any combination comprising at least one of the foregoing weakening systems.

3. The system as in claim 1, wherein the energy magnitude of the broad effect sub-system is lower than the energy magnitude of electroporation systems without the narrow effect sub-system whereby random pore opening occur.

4. The system as in claim 1, wherein the area of the broad effect sub-system encompasses an area larger than the desired pore size.

5. The system as in claim 1, wherein the area of the broad effect sub-system encompasses the membrane of a cell.

6. The system as in claim 1, wherein the area of the broad effect sub-system encompasses membranes of an array of cells.

7. The system as in claim 1, wherein the area of the broad effect sub-system encompasses a region of a membrane.

8. The system as in claim 1, wherein the narrow effect sub-system is selected from the group of position localization systems consisting of laser beams, electrode tips, or any combination comprising at least one of the foregoing position localization systems.

9. The system as in claim 1, wherein the area of the narrow effect sub-system corresponds to the dimensions of the pore opening.

10. The system as in claim 1, wherein the pore has sub-micron dimensions.

11. The system as in claim 1, wherein the pore has dimensions of about 100 nanometers or less.

12. A controllable electroporation system comprising:
    a broad effect sub-system for providing broad energy to the membrane and
    a narrow effect sub-system for providing narrow energy to the membrane,
    wherein a pore is opened when both the broad effect sub-system and the narrow effect sub-system are activated.

13. A method for controllably opening a pore in a membrane comprising:
    directing broad energy to the membrane and
    directing narrow energy to the membrane,
    wherein a pore is opened or created at a position corresponding to the position of the narrow energy.

14. The method as in claim 13, wherein the broad energy is selected from the group of energy systems consisting of electric fields, microwave energy, other electromagnetic radiation, low energy laser beams, or any combination comprising at least one of the foregoing energy systems.

15. The method as in claim 13, wherein the energy magnitude of the broad energy is lower than the energy magnitude of electroporation systems without the narrow effect sub-system whereby random pore opening occur.

16. The method as in claim 13, wherein the area of the broad energy encompasses an area larger than the desired pore size.

17. The method as in claim 13, wherein the area of the broad energy encompasses the membrane of a cell.

18. The method as in claim 13, wherein the area of the broad energy encompasses membranes of an array of cells.

19. The method as in claim 13, wherein the area of the broad energy encompasses a region of a membrane.

20. The method as in claim 13, wherein the narrow energy is selected from the group of position localization energy systems consisting of laser beams, electrode tips, or any combination comprising at least one of the foregoing position localization energy systems.

21. The method as in claim 13, wherein the area of the narrow energy corresponds to the dimensions of the pore opening.

22. The method as in claim 13, wherein the pore has sub-micron dimensions.

23. The method as in claim 13, wherein the pore has dimensions of about 100 nanometers or less.

24. A cell pore opening system comprising:
    a microrobotic device for holding a cell and
    a system as in claim 1 for controllably opening a pore in the cell.

25. The cell pore opening system as in claim 24, wherein the broad effect sub-system comprises an electrode plate and a switchable voltage source.

26. The cell pore opening system as in claim 24, wherein the narrow effect sub-system comprises a laser.

27. A cell pore macromolecule system comprising:
microrobotic device for holding a cell;
a system as in claim 1 for controllably opening a pore in the cell; and
a macromolecule injection device for injecting a macromolecule into the cell via the pore.

28. A method of opening a cell pore comprising:
holding a cell and
applying the method of claim 13 for controllably opening a pore in the cell.

29. A method of introducing a macromolecule in a cell comprising:
holding a cell;
applying the method of claim 13 for controllably opening a pore in the cell; and
introducing the macromolecule in the cell via the pore.

30. A system for filtering molecules or macromolecules comprising:
a plurality of membrane layers, each membrane layer including a system as in claim 1 for controllably opening a pore in the cell, each membrane layer opened to a different size to create a pore size gradient.

31. A system for filtering molecules or macromolecules comprising:
a plurality of membrane layers,
a broad effect sub-system associated with each membrane layer,
wherein each layer includes a position having a defect whereby said position is closed without activation of the broad effect sub-system and said position is opened upon activation of the broad effect sub-system.

32. The system as in claim 31, wherein said defect at each layer controls the size of the pore.

33. The system as in claim 31, wherein the magnitude of the energy of the broad effect sub-system controls the size of the pore.

34. A system for filtering molecules or macromolecules comprising:
a membrane layer including a system as in claim 1 for controllably opening a pore in the cell,
wherein the narrow effect energy sub-system comprises an array of narrow effect energy sub-sub-systems.

35. A system for filtering molecules or macromolecules comprising:
a membrane layer including a system as in claim 1 for controllably opening a pore in the cell,
wherein the narrow effect energy sub-system comprises an array of lasers.

36. A system for filtering molecules or macromolecules comprising:
a membrane layer including a system as in claim 1 for controllably opening a pore in the cell,
wherein the narrow effect energy sub-system comprises a beam steering device associated with a source of electromagnetic energy.

37. A controllable pore opening device comprising:
a bilayer cell membrane;
a laser beam source; and
an electric field source,
wherein a laser beam from laser beam source is applied to a position on the bilayer cell membrane to define a location of a pore opening and an electric field from the electric field source source is applied to open the pore.

38. The controllable pore opening device as in claim 37, wherein the bilayer cell membrane comprising phospholipid.

39. The controllable pore opening device as in claim 37, whereby the laser beam excites the molecules in the locale thereby reducing the amount of energy required from the electric field to open the pores, wherein the electric field may be weaker than an electric field value required to open the pores in absence of the laser beam.

40. A filter device comprising the controllable pore opening device as in claim 37.

41. A separation device comprising multiple filters as in claim 40 stacked together with different voltages applied to each filter thereby differing the pore size.

42. A filter device as in claim 40, wherein laser beam source is capable of directing a laser beam to a plurality of locations on the membrane thereby defining different locations for pore openings when electric field is applied.

43. A filter device as in claim 42, wherein pore size is varied by properties of the membrane or by variation in level of electric field, further comprising a plurality of containers associated with intended locations on the membrane for application of the laser beam.

44. A method of separating particles comprising
providing a bilayer membrane;
directing a laser beam to a position on the membrane;
applying an electric field to open a pore at the position on the membrane, whereby particles smaller than the pore size will be separated.

45. A method of separating particles comprising
providing a plurality of bilayer membranes in a stack;
directing a laser beam to a position on the membrane;
applying a separate electric field to each membrane to open pores in each membrane.

46. A method as in claim 45, wherein the electric field to at least one of the plurality of membranes is varied to change the opening size.

47. A method of separating particles comprising
providing a bilayer membrane;
directing the laser beam to a first position on the membrane;
applying an electric field to open a pore a the first position on the membrane,
whereby particles smaller than the first pore size will be separated and collected in a first container,
directing the laser beam to a second position on the membrane;
applying an electric field to open a pore a the second position on the membrane,
whereby particles smaller than the second pore size will be separated and collected in a second container.

48. A filter device comprising the controllable pore opening device as in claim 38.

49. A separation device comprising multiple filters as in claim 48 stacked together with different voltages applied to each filter thereby differing the pore size.

50. A filter device as in claim 48, wherein laser beam source is capable of directing a laser beam to a plurality of locations on the membrane thereby defining different locations for pore openings when electric field is applied.

51. A filter device as in claim 50, wherein pore size is varied by properties of the membrane or by variation in level of electric field, further comprising a plurality of containers associated with intended locations on the membrane for application of the laser beam.

* * * * *